United States Patent [19]

Goedecke et al.

[11] 4,217,451

[45] Aug. 12, 1980

[54] PROCESS FOR THE RECOVERY OF SOLID CYANURIC CHLORIDE (B)

[75] Inventors: Ralf Goedecke, Rodenbach; Uwe Kurandt, Frankfurt; Rolf Möller, Babenhausen, all of Fed. Rep. of Germany

[73] Assignee: Deutsche Gold- und Silber-Scheideanstalt vormals Roessler, Frankfurt, Fed. Rep. of Germany

[21] Appl. No.: 66,827

[22] Filed: Aug. 15, 1979

[30] Foreign Application Priority Data

Oct. 5, 1978 [DE] Fed. Rep. of Germany ....... 2843378

[51] Int. Cl.$^2$ ............................................ C07D 251/28
[52] U.S. Cl. ..................................................... 544/190
[58] Field of Search ......................................... 544/190

[56] References Cited

U.S. PATENT DOCUMENTS

| | | | |
|---|---|---|---|
| 3,179,662 | 4/1965 | Zinsstag et al. | 544/190 |
| 3,256,070 | 6/1966 | Trickey | 23/294 |
| 3,818,002 | 6/1974 | Goelz et al. | 544/190 |
| 3,925,377 | 12/1975 | Geiger et al. | 260/248 |
| 4,038,276 | 7/1977 | Geiger et al. | 260/248 |

FOREIGN PATENT DOCUMENTS

| | | |
|---|---|---|
| 1542066 | 3/1970 | Fed. Rep. of Germany. |
| 2337673 | 7/1973 | Fed. Rep. of Germany. |
| 2332636 | 1/1975 | Fed. Rep. of Germany. |
| 2537673 | 2/1977 | Fed. Rep. of Germany. |
| 2627880 | 12/1977 | Fed. Rep. of Germany. |

OTHER PUBLICATIONS

Allman, "Enzyklopadie der technischen Chemie", 3rd Ed., (1954) vol. 5, pp. 624–625.
Schellenberg, *Chemie, Ing. Tech.*, 38th year, (1966) No. 3, pp. 342–346.

*Primary Examiner*—John M. Ford
*Attorney, Agent, or Firm*—Cushman, Darby & Cushman

[57] ABSTRACT

Solid cyanuric chloride is recovered by a process of spraying in the presence of a cooling medium liquid cyanuric chloride which preferably is freed from chlorine and cyanogen chloride, the cyanuric chloride is sprayed with the aid of known spraying apparatus into a separation container optionally with a propellant, while simultaneously with the cyanuric chloride spraying a liquid cooling medium through a second spraying apparatus separate from the first spraying apparatus, withdrawing the solidified cyanuric chloride from the separatory container and drawing off the resulting now gaseous cooling medium containing cyanuric chloride from the lower portion of the separatory container.

16 Claims, 1 Drawing Figure

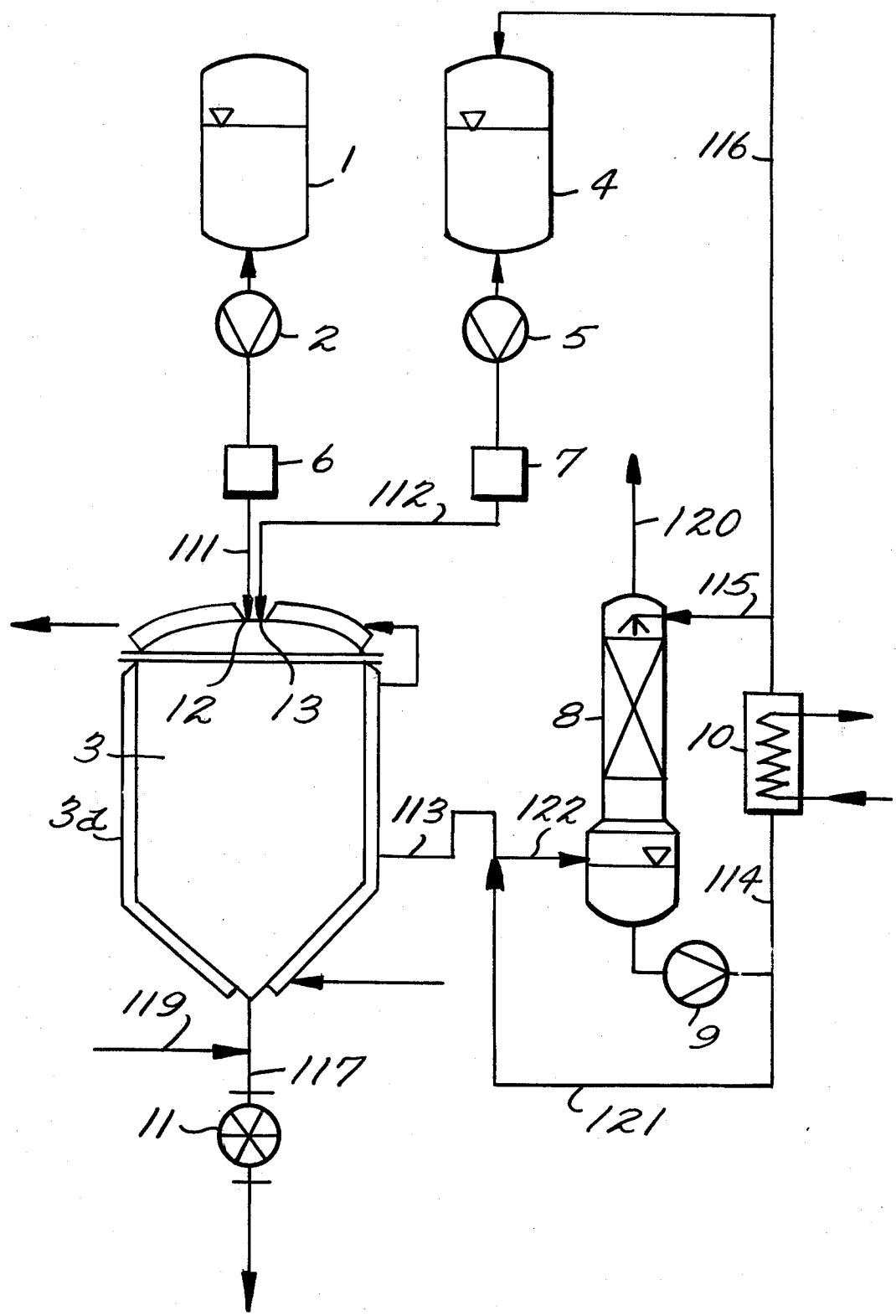

PROCESS FOR THE RECOVERY OF SOLID CYANURIC CHLORIDE (B)

BACKGROUND OF THE INVENTION

Cyanuric chloride which is recovered by trimerization of cyanogen chloride with the help of catalyst, above all activated carbon, as is known is a very interesting intermediate product for various industrial sectors such as the production of dyestuffs and products for the textile industry, as well as for pharmaceuticals, products for agriculture as well as for the synthetic resin, rubber and explosives industries.

As is known after the trimerization cyanuric chloride is obtained in gaseous form together with unreacted cyanogen chloride and chlorine as well as byproducts.

For a long time, it was customary to convert this gaseous reaction mixture directly into solid cyanuric chloride, e.g., by conducting the gaseous mixture into a chamber cooled from the outside (see Ullmann, Enzyklopadie der technischen Chemie, 3rd, Edition, 1954, Volume 5, pages 624–625 and 4th Edition, 1975, Volume 9, page 652).

It has also been passed into a ball mill cooled with water according to the process of Trickey U.S. Pat. No. 3,256,070.

Solid cyanuric chloride generally is obtained in powdery form and until now was predominantly further processed in this form.

A disadvantage of the solid cyanuric chloride, however, is that it is frequently not simple to handle.

In the recovery of solid cyanuric chloride by direct desublimation of the reaction gases in separation chambers it was a disadvantage that it was difficult to produce fine-grained products with a narrow particle spectrum.

Thus a part of the cyanuric chloride frequently deposited in the form of coarse crystals on the walls and installations of the desublimation chambers which then had to be mechanically knocked off and had to be reduced to the smaller grain diameter in a subsequent step, entirely apart from the interruption in operating required thereby.

The net result was that residues of chlorine and cyanogen chloride were still enclosed in the final product as a result of which not only caking occurred but also the storage and further processing of the cyanuric chloride was made more difficult.

Furthermore because of corrosive reaction gas constituents chlorine and cyanogen chloride there is also the danger of corrosions in the separatory and discharge aggregates.

Therefore there were endeavors to find other ways for the recovery of cyanuric chloride from the reaction gases.

Thus there are processes known in which the cyanuric chloride contained in the reaction gas is liquified before the solidification and then to convert it into fine-grained, solid form by spraying whereby only ⅓ of the heat of desublimation was drawn off, see Geiger German Pat. No. 2,537,673 and related Geiger U.S. Pat. No. 4,038,276.

In this process the heat of melting is drawn off by inert gases brought into the separation container. By the use of the liquid cyanuric chloride chlorine and cyanogen chloride is removed before the solidification.

The precipitated solid cyanuric chloride was fine particled but the use of the inert gas as cooling medium required additional processing steps for discharging the cyanuric chloride from the inert gas.

The purpose of the invention is to provide a process for the recovery of cyanuric chloride in fine-grain (or fine particle) form with the aimed at narrow particle spectrum without large expense for apparatus.

SUMMARY OF THE INVENTION

It has now been found that cyanuric chloride can be recovered in fine grain (fine particle) form with a narrow particle size distribution by spraying liquid cyanuric chloride if liquid cyanuric chloride, which preferably is free from chlorine and cyanogen chlorine is sprayed with the help of a first conventional spraying apparatus into a separatory container in a given case with a propellant while simultaneously with the cyanuric chloride spraying a liquid cooling medium through a second spraying apparatus separate from the first spraying apparatus, withdrawing the solidified cyanuric chloride from the separatory container and drawing off the resulting now gaseous cooling medium containing cyanuric chloride from the lower portion of the separatory container.

The recovery of liquid cyanuric chloride is known of itself. Preferred are the processes of Geiger German Pat. No. 2,332,636 or related Geiger U.S. Pat. No. 3,925,377 the entire disclosure of the Geiger U.S. patent is hereby incorporated by reference and relied upon.

As spraying apparatus there are suited in principle any type of distribution organ, as e.g. rotary plates, unary or binary nozzles.

By changing the number of revolutions in using a rotary plate, by varying the inlet pressure in a unary nozzle and by changing the liquid-gas ratio in the binary nozzle the product quality sought can be produced, which is distinguished by very narrow particle fractions which is a particular advantage for the further processing of the product.

The advantage of a unary nozzle is in that the amount of waste gas stream to be removed from the system is kept to a minimum, the advantage of the binary nozzle is in the greater throughput per nozzle since in this case larger bore diameters are used than with the unary nozzles while at the same quality of product.

Besides through the use of the larger bore diameter the danger of clogging is practically avoided.

A smaller amount of waste gas is also obtained through the use of the liquid binary nozzles in which the two media to be sprayed, i.e., the liquid and the gaseous medium, before leaving the nozzle outlet cross section are mixed together homogeneously, the mixture accelerated in the nozzles, and this mixture leaves the nozzle cross section with the speed of sound, whereby the average drop diameter of the sprayed molten cyanuric chloride and therewith the particle size of the solid cyanuric chloride can be regulated through selection of the ratio of the composition of the liquid and gaseous portion of the mixed media.

As is known the kinetic energy of the liquid, which in turn again depends on the exerted pressure (inlet pressure) and grows with increasing inlet pressure is responsible for the acceleration of the mixture.

Besides it is known that in a moving liquid pressure surges occur which act counter to the direction of flow.

From a fixed velocity of flow upward the pressure surge remains constant and no longer acts against the direction of flow, namely when this velocity is the same as the velocity of sound of the homogeneous mixture of the liquid and gaseous portion.

These types of binary nozzles are known of themselves, e.g. in Meszaros German AS No. 1,542,066, Chawla German OS No. 3,627,880, as well as the general principles in Schellenberg, "Chemie-Ing.-Techn.", 38th year, 1966 No. 3 pages 342–346.

With preselected nozzle geometry and a desired cyanuric chloride composition flow for establishment of a fixed particle spectrum the composition ratio of the mixed media of liquid and gaseous phase belonging thereto are determined by a small scale test.

Preferred are particle spectra in which the particle diameter is up to about 98% below 63$\mu$.

To solidify the sprayed cyanuric chloride the heat is drawn by vaporization of the atomized cooling medium.

As cooling liquids there can be employed all solvents or mixtures of solvents that are inert to cyanuric chloride and boil between 30° and 60° C., such as chlorinated hydrocarbons or fluorochlorinated hydrocarbons.

Especially preferred are methylene chloride and trichlorotrifluoroethane. Other suitable solvents are, for example, ethylidene chloride, propyl chloride, isopropyl chloride and sec. butyl chloride.

Preferably for dissemination of the cooling-medium unary nozzles are used.

The sprayed cyanuric chloride enters a separatory container in which the droplets, as mentioned above, are solidified by crystallization. There are employed conventional separatory containers, which preferably are jacketed.

Preferably the lower portion of the separatory container is conical. A weak inert gas flow, e.g. air or nitrogen, can be led counter to the product.

By this means there is removed the atmosphere found in the product, i.e., between the cyanuric chloride particles. The atmosphere contains both cyanuric chloride vapor and solvent vapor and by the indicated procedure there is prevented a condensation of the solvent during the emptying and storage of the product.

The temperature in the separatory container generally is between 65° and 80° C., preferably above the boiling temperature of the cooling media used.

To maintain the necessary temperature there are heated the entire walls of the container, including the upper portion.

The heating can be carried out with the customary heating media, such as e.g. heat carrier oils or vapor or by electrical energy.

The gaseous cooling medium containing cyanuric chloride which leaves the container can either be destroyed or worked up according to known process, e.g. according to the process of German Pat. No. 2,337,673.

A preferred and particularly environmentally desirable method of working up consists of leading the gaseous cooling agent which contains cyanuric chloride and accruing in the lower part of the separatory container into a washing column where it is condensed in countercurrent flow with the cooling medium added into the separatory container.

Thereby the cyanuric chloride dissolves in the condensed medium.

The cyanuric chloride containing cooling liquid is now preferably again returned into the solvent container and employed again as cooling liquid.

By choosing a cooling medium which has a particularly high dissolving power for cyanuric chloride, as, e.g. methylene chloride or trichlorotrifluoroethane, as well as the mentioned return of the cooling liquid into the separatory container through which the dissolved cyanuric chloride is continuously again separated in solid form from the cooling medium in solid form, there is never reached or exceeded the saturation of the cooling medium in cyanuric chloride in the sump of the wash column.

In this manner the losses in the amount of a cooling medium added one time are practically zero.

Both with unary nozzles and binary nozzles, which operate with reduced amounts of propellant gas, as mentioned, the amount of waste gas can be limited to a minimum.

Because of the very slight loading of waste gases with cyanuric chloride which, as mentioned, is practically zero, there can be eliminated a separation of solid and the apparatus expensive for purification of gas can be held small.

The advance in the art of the process of the invention, as already mentioned, is first in the possibility to get cyanuric chloride with particularly well regulatable particle spectra, preferably with a high particle portion in fine form.

Additionally, by using a liquid cooling medium in place of a gaseous cooling medium there is avoided the danger of a clogging of the cooling aggregate in cooling.

It is also very significant that the cooling medium can be recycled and thereby there are formed practically no losses of cooling agent.

The resulting solid product has particularly good pourability, i.e., the product does not cake together; which is particularly advantageous in the withdrawing, storage and further processing.

Additionally, the product has the known purity of 99% and is practically free from chlorine and cyanogen chloride.

The losses of cyanuric chloride through the waste gas leaving the apparatus are practically zero since the waste gas is washed free from cyanuric chloride by the condensed cooling medium.

The yield of cyanuric chloride therefore is practically quantitative.

BRIEF DESCRIPTION OF THE DRAWING

The single FIGURE of the drawings is a schematic illustration of a process for carrying out the process of the invention.

Referring more specifically to the drawings the liquid cyanuric chloride is supplied from the storage container 1 via the pump 2 through the filter 6 and through the tubular conduit 111 to the separatory container 3 and atomized by means of an atomizing apparatus 12 (here: a unary nozzle) and simultaneously there is supplied (and in this case sprayed) to the separatory container 3 via one or more nozzles 13 as cooling liquid solvent from the storage container 4 via the pump 5 through the filter 7 and the tubular conduit 112.

The entire separatory container is furnished with a double jacket 3 through which flows a heating liquid that keeps the walls of the separatory container 3 at a temperature above the boiling temperature of the cooling liquid.

The solidified cyanuric chloride particles collect in the conically constructed portion of the separatory container 3 and are discharged from here via tubular conduit 117 through the bucket wheel valve 11. In order to remove the vaporous atmosphere heavily loaded with solvent and cyanuric chloride between the crystallized cyanuric chloride particles in the lower portion of the separatory container 3 inert gas is led via the tubular conduit 119 into the outlet of separatory container 3.

The waste gas saturated with solvent, containing cyanuric chloride vapor and inert gas as well as being laden with cyanuric chloride dust flows via the tubular conduit 113 into the wash column 8 sprayed with solvent.

The overflow tube 113 in the portion 122 which drops down to the wash column between the separatory container 3 and the wash column pump 8 is sprayed internally with solvent via the tubular conduit 121.

The cooling liquid vapor saturated with cyanuric chloride is condensed in the wash column 8 in countercurrent flow with the same cooling liquid.

The condensed solvent with the dissolved portion of cyanuric chloride is supplied from the sump of the wash column 8 as a circulatory stream by means of the pump 9 through the tubular conduit 114 via the cooler 10 and the tubular conduit 116 to the storage container 4.

A partial stream is recycled by being pumped with the help of the pump 9 via the tubular conduit 115 through the wash column 8 in countercurrent flow to the gas stream.

The waste gas purified consisting essentially of inert gas with traces of solvent flows via the tubular conduit 120 from the wash column 8 into a waste gas purification stage (not shown).

Unless otherwise indicated all parts and percentages are by weight.

The process can comprise, consist essentially of or consist of the steps set forth and the materials employed can comprise, consist essentially of or consist of those set forth.

DESCRIPTION OF THE PREFERRED EMBODIMENTS

Example 1

There were sprayed into the separatory container 3 (diameter 0.8 meter, height 2.5 meters) from the storage container 1 with the help of pump 2 through the filter 6 via the tubular conduit 111 through the unary nozzle 12 with a bore diameter of 0.6 mm hourly 7.5 kg of liquid cyanuric chloride with a temperature of 170° C. and a pressure of 6.0 bar. Simultaneously there were sprayed into the separatory container 3 from the storage container 4 with the help of the pump 5 through the filter 7 via the tubular conduit 112 through the nozzle 13 hourly 12.9 kg of trichlorotrifluoroethane with a temperature of 20° C. at a pressure of 1.5 bar. The solvent vaporized here while taking up the heat of crystallization of the cyanuric chloride.

The solvent and cyanuric chloride containing gas leaving the separatory container 3 via tubular conduit 113 at 50° C. was condensed in the wash column 8 and simultaneously washed free of cyanuric chloride with 0.08 m³/h of trichlorotrifluoroethane in countercurrent flow. The waste gas of 0.2 Nm³/h flowed via the conduit 120 into a waste gas washing system (not shown). The condensed solvent in an amount of 12.9 kg/h with a temperature of 35° C. and containing cyanuric chloride was pumped with the help of the pump 9 via the tubular conduit 114 through the cooler 10, where there occurred a cooling to 20° C., through the tubular conduit 116 into the storage container 4. From here the cooling liquid was again supplied to the nozzles 13. Simultaneously a partial stream of solvent of 133.5 kg/h was recycled by means of the pump 9 through the tubular conduit 115 via the condenser 8 countercurrent to the flow of gas.

There was obtained in the conical portion of the separatory container 3 solid cyanuric chloride having the following particle size distribution:

| | |
|---|---|
| >100μ | 0 weight % |
| 63–100μ | 1.6 weight % |
| 40–63μ | 37.7 weight % |
| 33–40μ | 23.40 weight % |
| <33μ | 37.3 weight % |

The fine divided cristalline product was handled as in example 2. The nitrogen volume flow was of 0,2Nm³/h.

EXAMPLE 2

There were sprayed into the separatory container 3 (diameter 0.8 m, height 2.5 m) from the storage container 1 with the help of pump 2 through the filter 6 via the tubular conduit 111 through the unary nozzle 12 with a bore diameter of 1.0 mm hourly 30 kg of liquid cyanuric chloride with a temperature of 170° C. and a pressure of 5.0 bar. Simultaneously there were sprayed into the separatory container 3 from the storage container 4 with the help of the pump 5 through the nozzle 13 hourly 21 kg of methylene chloride with a temperature of 20° C. at a pressure of 3.0 bar. The solvent vaporized here while taking up the heat of crystallization of the cyanuric chloride.

The solvent and cyanuric chloride containing gas leaving the separatory container 3 via tubular conduit 113 at 50° C. was condensed in the washing column 8 and simultaneously washed free of cyanuric chloride with 0.34 m³/h of methylene chloride in countercurrent flow. The waste gas of 0.5 Nm³/h flowed via the tubular conduit 120 into a waste gas washing system (not shown). The condensed solvent in an amount of 21 kg/h with a temperature of 35° C. and containing cyanuric chloride was pumped with the help of the pump 9 via the tubular conduit 114 through the cooler 10, where there occurred a cooling to 20° C., through the tubular conduit 116 into the storage container 4. From here the cooling liquid was again supplied to the nozzles 13. Simultaneously a partial stream of solvent of 460 kg/h was recycled by means of the pump 9 through the tubular conduit 115 via the condenser 8 countercurrent to the flow of gas.

There was obtained in the conical portion of the separatory container 3 solid cyanuric chloride having the following particle size distribution:

| | |
|---|---|
| >160μ | 0.4 weight % |
| 100–160μ | 12.0 weight % |
| 63–100μ | 30.0 weight % |
| 40–63μ | 9.2 weight % |
| 33–40μ | 11.4 weight % |
| <33μ | 37 weight % |

The finely divided crystalline product was carried out via the tubular conduit 117 by means of bucket wheel valve 11.

There was supplied through tubular conduit 119 a nitrogen volume flow of 0.5 Nm³/h into the outlet of the container 3.

EXAMPLE 3

There were sprayed into the separatory container 3 (diameter 0.8 m, height 2.5 m) from the storage container 1 with the help of pump 2 through the filter 6 via the tubular conduit 111 through the binary nozzle 12 with a bore diameter of 3.0 mm hourly 130 kg of liquid cyanuric chloride with a temperature of 170° C. and a pressure of 4.0 bar. Simultaneously there were supplied 1.2 Nm³/h of compressed air at a pressure of 4.0 bar and a temperature of 180° C. to the binary nozzle. Furthermore, there were sprayed into the separatory container 3 from the storage container 4 with the help of the pump 5 through the filter 7 via the tubular conduit 112 through the nozzle 13 hourly 223.6 kg of trichlorotrifluoroethane with a temperature of 20° C. at a pressure of 1.5 bar. The solvent vaporized here while taking up the heat of crystallization of the cyanuric chloride. The solvent and cyanuric chloride containing gas leaving the separatory container 3 via tubular conduit 113 at 50° C. was condensed in the washing column 8 and simultaneously washed free of cyanuric chloride with 1.45 m³/h of trichlorofluoroethane in countercurrent flow. The waste gas of 1.7 Nm³/h flowed via the tubular conduit 120 into a waste gas washing system (not shown). The condensed solvent in an amount of 223.6 kg/h with a temperature of 35° C. and containing cyanuric chloride was pumped with the help of the pump 9 via the tubular conduit 114 through the cooler 10, where there occurred a cooling to 20° C., through the tubular conduit 116 into the storage container 4. From here the cooling liquid was again supplied to the nozzles 13. Simultaneously a partial stream of solvent of 2314.7 kg/h was recycled by means of the pump 9 through the tubular conduit 115 via the condenser 8 countercurrent to the flow of gas.

There was obtained in the conical portion of the separatory container 3 solid cyanuric chloride having the following particle size distribution:

| | |
|---|---|
| <50μ | 95.6 weight % |
| 50–70μ | 2.6 weight % |
| 70–100μ | 1.0 weight % |
| 100–160μ | 0.4 weight % |
| >160μ | 0.4 weight % |

The finely divided crystalline product was carried out via the tubular conduit 117 by means of bucket wheel valve 11.

There was supplied through tubular conduit 119 a flow volume of nitrogen of 0.5 Nm³/h into the outlet of container 3.

EXAMPLE 4

There were sprayed into the separatory container 3 (diameter 0.8 m, height 2.5 m) from the storage container 1 with the help of pump 2 through the filter 6 via the tubular conduit 111 through the binary nozzle 12 with a bore diameter of 3.0 mm hourly 130 kg of liquid cyanuric chloride with a temperature of 170° C. and a pressure of 5.5 bar. Simultaneously there were supplied 2.5 Nm³/h of compressed air at a pressure of 5.5 bar and a temperature of 180° C. to the binary nozzle. Furthermore, there were sprayed into the separatory container 3 from the storage container 4 with the help of pump 5 through the filter 7 via the tubular conduit 112 through the nozzle 13 hourly 91 kg of methylene chloride with a temperature of 20° C. at a pressure of 1.5 bar. The solvent vaporized here while taking up the heat of crystallization of the cyanuric chloride. The solvent and cyanuric chloride containing gas leaving the separatory container 3 via tubular conduit 113 at 50° C. was condensed in the washing column 8 and simultaneously washed free of cyanuric chloride with 1.5 m³/h of methylene chloride in countercurrent flow. The waste gas of 3.2 Nm³/h flowed via the tubular conduit 120 into a waste gas washing system (not shown). The condensed solvent in an amount of 91 kg/h with a temperature of 35° C. and containing cyanuric chloride was pumped with the help of the pump 9 via the tubular conduit 114 through the cooler 10, where there occurred a cooling to 20° C., through the tubular conduit 116 into the storage container 4. From here the cooling liquid was again supplied to the nozzles 13. Simultaneously a partial stream of solvent of 1995 kg/h was recycled by means of the pump 9 through the tubular conduit 115 via the condensor 8 countercurrent to the flow of gas.

There was obtained in the conical portion of the separatory container 3 solid cyanuric chloride having the following particle size distribution:

| | |
|---|---|
| <50μ | 98 weight % |
| 50–70μ | 1.6 weight % |
| 70–100μ | 0.4 weight % |

The finely divided crystalline product was carried out via the tubular conduit 117 by means of bucket wheel valve 11.

There was supplied through tubular conduit 119 a flow volume of nitrogen of 0.5 Nm³/h into the outlet of container 3.

There is hereby incorporated by reference the entire disclosure of German priority application P2843378.5-44.

What is claimed is:

1. A process for recovering solid cyanuric chloride comprising spraying liquid cyanuric chloride in the presence of a cooling medium, said process including the steps of spraying the liquid cyanuric chloride with the aid of a first spraying means into a separatory container, simultaneously spraying a liquid cooling medium through a second spraying means into said container, withdrawing the solidified cyanuric chloride from said container and drawing off the resulting gaseous cooling medium containing cyanuric chloride from the lower portion of said container.

2. The process according to claim 1 wherein the liquid cyanuric chloride is substantially free from chlorine and cyanogen chloride and the liquid cyanuric chloride is sprayed with the aid of a propellant gas.

3. The process according to claim 2 comprising spraying the liquid cyanuric chloride through a unary nozzle.

4. The process according to claim 2 comprising spraying the liquid through a binary nozzle.

5. The process according to claim 4 comprising homogeneously mixing the media in the binary nozzle and accelerating the mixture in the nozzle to the required nozzle exit velocity.

6. The process according to claim 5 wherein the mixture is accelerated in the nozzle to an exit speed of the velocity of sound.

7. The process of claim 2 comprising supplying the gaseous cooling medium containing cyanuric chloride obtained in the lower portion of the separatory container to a washing column, condensing said gaseous cooling medium in said washing column in countercurrent flow to liquid cooling medium.

8. The process according to claim 7 including the step of returning the condensed cooling liquid containing cyanuric chloride to the separatory container.

9. The process according to claim 8 comprising supplying a weak flow of inert gas in the separatory container countercurrently to the product moving downwardly through said container.

10. The process of claim 9 comprising wherein the inert gas is introduced through the product outlet conduit.

11. The process of claim 9 wherein the waste gas with the gaseous cooling medium and propellant gas leaving the separatory container is washed free from cyanuric chloride in countercurrent flow with the condensed cooling medium in the washing medium.

12. The process of claim 11 wherein the cooling medium is a halogenated aliphatic hydrocarbon boiling between 30° to 60° C. at atmospheric pressure.

13. The process of claim 12 wherein the cooling medium is methylene chloride or trichlorotrifluoroethane.

14. The process of claim 1 wherein the cooling medium is a halogenated aliphatic hydrocarbon boiling between 30° to 60° C. at atmospheric pressure.

15. The process of claim 12 comprising maintaining the walls of the separatory container at a temperature about the boiling point of the cooling mixture.

16. The process of claim 7 comprising continuously internally spraying the overflow conduit between the separatory container and washing column for removing the gaseous cyanuric chloride containing cooling medium with liquid cooling medium.

* * * * *